United States Patent
Wang et al.

(10) Patent No.: US 11,306,151 B2
(45) Date of Patent: Apr. 19, 2022

(54) ANTI-TIP-1 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Joshua Oaks, San Diego, CA (US)

(73) Assignee: Phanes Therapeutics, Inc., San Diego, CA (US)

( * ) Notice: Subject to any disclaimer, the term of this patent is extended or adjusted under 35 U.S.C. 154(b) by 37 days.

(21) Appl. No.: 15/733,554

(22) PCT Filed: Mar. 6, 2019

(86) PCT No.: PCT/US2019/020867
§ 371 (c)(1),
(2) Date: Aug. 26, 2020

(87) PCT Pub. No.: WO2019/173417
PCT Pub. Date: Sep. 12, 2019

(65) Prior Publication Data
US 2020/0399396 A1 Dec. 24, 2020

Related U.S. Application Data

(60) Provisional application No. 62/640,123, filed on Mar. 8, 2018.

(51) Int. Cl.
*C07K 16/00* (2006.01)
*G01N 33/574* (2006.01)
*C07K 16/30* (2006.01)

(52) U.S. Cl.
CPC ....... *C07K 16/30* (2013.01); *G01N 33/57492* (2013.01); *C07K 2317/31* (2013.01); *C07K 2317/56* (2013.01); *C07K 2317/565* (2013.01)

(58) Field of Classification Search
CPC ............... C07K 16/30; C07K 2317/31; C07K 2317/56; C07K 2317/565; G01N 33/57492; A61P 35/00
See application file for complete search history.

(56) References Cited

U.S. PATENT DOCUMENTS

| 2003/0018004 A1 | 1/2003 | Kingsman |
| 2014/0316186 A1 | 10/2014 | Hallahan |

FOREIGN PATENT DOCUMENTS

| WO | 2001088546 | 11/2001 |
| WO | 2002022851 | 3/2002 |
| WO | 2013019730 | 2/2013 |
| WO | 2015116653 | 8/2015 |

OTHER PUBLICATIONS

Hallahan et al., "PO-0981: Activation of immune cells and enhanced efficacy of radiotherapy by anti-TIP1 antibodies in cancer", ESTRO 35, Radiotherapy and Oncology, (Apr. 29, 2016), vol. 119, No. 1, page S447, XP029692157.
Hallahan, D.E., "3130: Antibodies Targeted to Radiation Inducible Neoantigens in Cancer", (Oct. 1, 2011), vol. 81, No. 2, p. S751 (2 pages).
International Preliminary Report on Patentability issued in PCT/US2019/020867, dated Sep. 8, 2020, 6 pages.
International Search Report and Written Opinion issued in PCT/US2019/020867, dated May 19, 2010, 9 pages.
Kapoor et al., "5615: Antibodies targeting TIP1 enhance the efficacy of radiotherapy in lung cancer and glioblastoma", Proceedings of the American Association for Cancer Research Annual Meeting 2018, Cancer Research, (Apr. 14, 2018), vol. 78, No. 13 (1 page).
Wang et al., "TIP-1 Translocation onto the Cell Plasma Membrane Is a Molecular Biomarker of Tumor Response to Ionizing Radiation", PLoS One, (Aug. 11, 2010), vol. 5, No. 8, pp. 1-12, XP055642966.
Yan et al., "Anti-tax interacting protein-1 (TIP-1) monoclonal antibody targets human cancers", Oncotarget, (May 30, 2016), vol. 7, No. 28, pp. 43352-43362, XP055534053.
Alewine et al., "TIP-1 Has PDZ Scaffold Antagonist Activity(D)", Mol Biol Cell 17:4200-4211 (2006).
Besser et al., "Tip-1 induces filopodia growth and is important for gastrulation movements during zebrafish development", Dev Growth Differ 49:205-214(2007).
Han et al., "The PDZ protein TIP-1 facilitates cell migration and pulmonary metastasis of human invasive breast cancer cells in athymic mice", Biochem Biophys Res Commun 2012; 422:139-145.
Lee and Zheng, "PDZ domains and their binding partners: structurer, specificity, and modification", Cell Commun Signal 8:8 (2010) (18 pages).
Olalla et al., "The C-terminus of human glutaminase L mediates association with PDZ domain-containing proteins", FEBS Lett 2001; 488:116-122.
Zoetewey et al., "Promiscuous Binding at the Crossroads of Numerous Cancer Pathways: Insight from the Binding of Glutaminase Interacting Protein with Glutaminase L", Biochemistry 2011; 50:3528-3539.
Heping Yan et al., "Anti-tax interacting protein-1 (TIP-1) monoclonal antibody targets human cancers", Oncotarget, vol. 7, No. 28, May 30, 2016, pp. 43352-43362, XP055534053, DOI: 10.18632/oncotarget.9713.

(Continued)

*Primary Examiner* — Lei Yao
(74) *Attorney, Agent, or Firm* — Ice Miller LLP (57) ABSTRACT

Anti-TIP-1 antibodies and antigen-binding fragments thereof are described. Also described are nucleic acids encoding the antibodies, compositions comprising the antibodies, methods of producing the antibodies, and methods of using the antibodies for treating or preventing diseases, such as cancer.

11 Claims, 1 Drawing Sheet
Specification includes a Sequence Listing.

(56) References Cited

OTHER PUBLICATIONS

Kapoor et al., "Abstract 4599: Antibody targeting PDZ domain of TIP-1 induces proliferation arrest through AKT/mTOR signaling inhibition in lung cancer and glioblastoma", Cancer Research, vol. 77, Jul. 1, 2017, pp. 1-4, XP055842168, DOI: 10.1158/1538-7445. AM2017-4599 Retrieved from the Internet: URL:https://cancerres.aacrjournals.org/content/77/13_Supplement/4599.

Kapoor et al., "Monoclonal Antibody 2C6F3 Against Radiation-Inducible Cell Surface Tip-1 as a Novel Agent for Imaging and Targeting Tumors", International Journal of Radiation: Oncology Biology Physics, vol. 90, No. 1 , XP029058732, ISSN: 0360-3016, DOI: 10.1016/J.IJROBP.2014.05.2294.

ANTI-TIP-1 ANTIBODIES AND USES THEREOF

CROSS REFERENCE TO RELATED APPLICATIONS

This application is a Section 371 of International Application No. PCT/US2019/020867, filed Mar. 6, 2019, which published in the English language on Sep. 12, 2019 under International Publication No. WO 2019/173417 A1, which claims priority to U.S. Provisional Application No. 62/640,123, filed on Mar. 8, 2018. Each disclosure is incorporated herein by reference in its entirety.

FIELD OF THE INVENTION

This invention relates to monoclonal anti-TIP-1 antibodies, nucleic acids and expression vectors encoding the antibodies, recombinant cells containing the vectors, and compositions comprising the antibodies. Methods of making the antibodies, and methods of using the antibodies to treat diseases including cancer, are also provided.

REFERENCE TO SEQUENCE LISTING SUBMITTED ELECTRONICALLY

This application contains a sequence listing, which is submitted electronically via EFS-Web as an ASCII formatted sequence listing with a file name "065799_8_US2_Sequence Listing" and a creation date of Aug. 6, 2020 and having a size of 5 kb. The sequence listing submitted via EFS-Web is part of the specification and is herein incorporated by reference in its entirety.

BACKGROUND OF THE INVENTION

Tax-interacting protein 1 (TIP-1, also known as Tax1bp3 or glutaminase-interacting protein, GIP) is a PDZ (PSD-95/Discs large/ZO-1 homologous) domain-containing intracellular protein (124 amino acids in human and mouse). The single PDZ domain encompassing residues 13-112 of the 124-amino acid protein (Olalla, et al., FEBS Lett 2001; 488:116-122) is the only functional and structural unit that can be identified in TIP-1, suggesting that TIP-1 is unique among PDZ-containing proteins and may carry out its function solely through protein-protein interactions.

TIP-1 interacts with many intracellular proteins through the PDZ domain, including glutaminase L, β-Catenin, FAS, HTLV Tax, HPV E6, Rhotekin and Kir 2.3 (Zoetewey et al., Biochemistry 2011; 50:3528-3539). However, the precise biological function of TIP-1 remains unclear. Elevated TIP-1 expression was detected in human invasive breast cancer cells and shown to be linked to tumor cell adhesion, migration and pulmonary metastasis (Han et al., Biochem Biophys Res Commun 2012; 422:139-145).

Recently, it was found that TIP-1 is translocated to the surface of cancer cells upon induction by irradiation (Yan et al., Oncotarget 2016; 7:43352-43362), suggesting TIP-1 could be a cancer neoantigen upon induction. Thus, an anti-TIP-1 monoclonal antibody (mAb) can be used to target cancer cells with selectivity and to serve as a potential therapeutic.

BRIEF SUMMARY OF THE INVENTION

In one general aspect, the invention relates to isolated monoclonal antibodies or antigen-binding fragments thereof that bind TIP-1.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
a. SEQ ID NOs:3, 4, 5, 6, 7, and 8, respectively;
wherein the antibody or antigen-binding fragment thereof specifically binds TIP-1, preferably human TIP-1.

In certain embodiments, the isolated monoclonal antibody or antigen-binding fragment thereof comprises a heavy chain variable region having a polypeptide sequence at least 95% identical to SEQ ID NO:1, or a light chain variable region having a polypeptide sequence at least 95% identical to SEQ ID NO:2.

In certain embodiments, the isolated monoclonal antibody or antigen-binding fragment thereof comprises:
a. a heavy chain variable region having the polypeptide sequence of SEQ ID NO:1, and a light chain variable region having the polypeptide sequence of SEQ ID NO:2.

In certain embodiments, the isolated monoclonal antibody or antigen-binding fragment thereof is capable of inducing effector-mediated tumor cells lysis through antibody-dependent cellular cytotoxicity (ADCC) and/or complement-dependent cytotoxicity (CDC) by binding to TIP-1 on the cell surface, and/or mediating the recruitment of conjugated drugs, and/or forming a bispecific antibody with another monoclonal antibody or antigen-binding fragment thereof with cancer-killing effect.

In certain embodiments, the isolated monoclonal antibody or antigen-binding fragment thereof is chimeric.

In certain embodiments, the isolated monoclonal antibody or antigen-binding fragment thereof is human or humanized.

Also provided are isolated nucleic acids encoding the monoclonal antibodies or antigen-binding fragments thereof of the invention.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising the isolated monoclonal antibody or antigen-binding fragment thereof of the invention and a pharmaceutically acceptable carrier.

Also provided are methods of treating cancer in a subject in need thereof, comprising administering to the subject the pharmaceutical compositions of the invention. The cancer can be any liquid or solid cancer, for example, it can be selected from, but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Also provided are methods of producing the monoclonal antibody or antigen-binding fragment thereof of the invention. The methods comprise culturing a cell comprising a nucleic acid encoding the monoclonal antibody or antigen-binding fragment thereof under conditions to produce the monoclonal antibody or antigen-binding fragment thereof and recovering the antibody or antigen-binding fragment thereof from the cell or culture.

Also provided are methods of producing a pharmaceutical composition comprising the monoclonal antibody or antigen-binding fragment thereof of the invention. The methods comprise combining the monoclonal antibody or antigen-binding fragment thereof with a pharmaceutically acceptable carrier to obtain the pharmaceutical composition.

Also provided are methods of determining a level of TIP-1 in a subject. The methods comprise (a) obtaining a sample from the subject; (b) contacting the sample with an isolated monoclonal antibody or antigen-binding fragment thereof of the invention; and (c) determining a level of TIP-1 in the subject. The sample can, for example, be a tissue sample or a blood sample. The tissue sample can, for example, be a cancer tissue sample.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-TIP-1 antibodies and polynucleotides that encode them, TIP-1 polypeptides and TIP-1 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F.M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

Antibodies

The invention generally relates to isolated anti-TIP-1 antibodies, nucleic acids and expression vectors encoding the antibodies, recombinant cells containing the vectors, and compositions comprising the antibodies. Methods of making the antibodies, and methods of using the antibodies to treat diseases including cancer are also provided. The antibodies of the invention possess one or more desirable functional properties, including but not limited to high-affinity binding to TIP-1, high specificity to TIP-1, and the ability to inhibit tumor growth in animal models when administered alone or in combination with other anti-cancer therapies.

In a general aspect, the invention relates to isolated monoclonal antibodies or antigen-binding fragments thereof that specifically bind TIP-1.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to TIP-1 is substantially free of antibodies that do not bind to TIP-1). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on TIP-1 and the second epitope is located on PD-1, PD-L1, LAG-3, TIM-3, CTLA-4, EGFR, HER-2, CD19, CD20, CD33, CD47, CD73, apelin, DLL3, claudin 18.2 (CLDN18.2), FRa (folate receptor alpha), CD3 and/or other tumor associated immune suppressors or surface antigens.

As used herein, the term "TIP-1" refers to tax-interacting protein 1 (TIP-1, also known as Tax1bp3 or glutaminase-interacting protein, GIP), which is a PDZ (PSD-95/Discs large/ZO-1 homologous) domain-containing intracellular protein (124 amino acids in human and mouse) (Besser et al., Dev Growth Differ 49:205-214 (2007)). PDZ domains are small (80-100 residues) protein-protein interaction motifs that typically bind to the C-terminus of their partner proteins (Lee and Zheng, Cell Commun Signal 8:8 (2010)). The single PDZ domain, encompassing residues 13-112 of the 124-amino acid protein (Olalla, et al., FEBS Lett 488: 116-122 (2001)), is the only functional and structural unit that can be identified in TIP-1. TIP-1 is ubiquitously expressed in human tissues (Alewine et al., Mol Biol Cell 17:4200-4211 (2006)). TIP-1 interacts with many intracellular proteins through the PDZ domain, including glutaminase L, β-Catenin, FAS, HTLV Tax, HPV E6, Rhotekin and Kir 2.3 (Zoetewey et al., Biochemistry 50:3528-3539 (2011)), and may exert multiple biological functions. For example, by competing with the basolateral membrane mLin-7/CASK complex for interaction with the potassium channel Kir 2.3, TIP-1 inhibits the targeting of Kir 2.3 to polarized plasma membrane (Alewine et al., Mol Biol Cell 17:4200-4211 (2006)). Elevated TIP-1 expression was detected in human invasive breast cancer cells and shown to be linked to tumor cell adhesion, migration and pulmonary metastasis (Han et al., Biochem Biophys Res Commun 422:139-145 (2012)). TIP-1 is translocated to the surface of cancer cells upon induction by irradiation (Yan et al., Oncotarget 7:43352-43362 (2016)), suggesting TIP-1 could be a cancer neoantigen upon induction. An exemplary amino acid sequence of a human TIP-1 is represented by GenBank Accession No. 014907.2 (SEQ ID NO:9).

As used herein, an antibody that "specifically binds to TIP-1" refers to an antibody that binds to a TIP-1, preferably a human TIP-1, with a KD of $1\times10^{-7}$M or less, preferably $1\times10^{-8}$M or less, more preferably $5\times10^{-9}$ M or less, $1\times10^{-9}$M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

a. SEQ ID NOs:3, 4, 5, 6, 7, and 8, respectively; wherein the antibody or antigen-binding fragment thereof specifically binds TIP-1, preferably human TIP-1.

According to another particular aspect, the invention relates to an isolated monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to SEQ ID NO:1, or a light chain variable region having a polypeptide sequence at least 85%, preferably 90%, more preferably 95% or more, such as 95%, 96%, 97%, 98%, or 99% identical to SEQ ID NO:2. According to one preferred embodiment, the isolated monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2, respectively.

According to another particular aspect, the invention relates to an isolated monoclonal antibody or antigen-binding fragment thereof of the invention, comprising:

a. a heavy chain variable region having the polypeptide sequence of SEQ ID NO:1, and a light chain variable region having the polypeptide sequence of SEQ ID NO:2;

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:3, 4, 5, 6, 7, and 8, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

According to another particular aspect, the invention relates to an isolated monoclonal antibody or antigen-binding fragment thereof, wherein the antibody or antigen-binding fragment thereof is chimeric.

According to another particular aspect, the invention relates to an isolated monoclonal antibody or antigen-binding fragment thereof, wherein the antibody or antigen-binding fragment thereof is human or humanized.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorhexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of targeting TIP-1 on a cancer cell surface in a subject, the method comprising administering to the subject an isolated monoclonal antibody or antigen binding fragment thereof that specifically binds TIP-1 or a pharmaceutical composition of the invention. The TIP-1 monoclonal antibody or antigen-binding fragment thereof is capable of binding TIP-1 on a cancer cell surface in the subject. Binding of the anti-TIP-1 monoclonal antibody or antigen-binding fragment thereof to the translocated TIP-1 on the cell surface can allow for the recruitment of effector cells of the immune system, the complement system, and/or conjugated drugs to mediate cancer-killing activities in the subject. The anti-TIP-1 monoclonal antibody can, for example, form a bispecific antibody with another monoclonal antibody or antigen-binding fragment that can also mediate cancer-killing activities in the subject.

The functional activity of antibodies and antigen-binding fragments thereof that bind TIP-1 can be characterized by methods known in the art and as described herein. Methods for characterizing antibodies and antigen-binding fragments thereof that bind TIP-1 include, but are not limited to, affinity and specificity assays including Biacore, ELISA, and OctetRed analysis; binding assays to detect the binding of antibodies to TIP-1 on cancer cells by FACS. According to particular embodiments, the methods for characterizing antibodies and antigen-binding fragments thereof that bind TIP-1 include those described below.

In another general aspect, the invention relates to a method of treating a cancer in a subject in need thereof, comprising administering to the subject an isolated monoclonal antibody or antigen binding fragment thereof that specifically binds TIP-1 or a pharmaceutical composition of the invention. The cancer can, for example, be selected from but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

According to embodiments of the invention, the pharmaceutical composition comprises a therapeutically effective amount of an anti-TIP-1 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-TIP-1 antibodies or antigen-binding fragments thereof, a therapeutically effective amount means an amount of the anti-TIP-1 antibody or antigen-binding fragment thereof that modulates an immune response in a subject in need thereof.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, provided are compositions used in the treatment of a cancer. For cancer therapy, the compositions can be used in combination with another treatment including, but not limited to, a chemotherapy, an anti-CD20 mAb, an anti-TIM-3 mAb, an anti-LAG-3 mAb, an anti-CD73 mAb, an anti-CD47 mAb, an anti-apelin mAb, an anti-claudin18.2 mAb, an anti-DLL3 mAb, an anti-FRa mAb, an anti-CTLA-4 antibody, an anti-PD-L1 antibody, an anti-PD-1 antibody, a PD-1/PD-L1 therapy, other immuno-oncology drugs, an antiangiogenic agent, a radiation therapy, an antibody-drug conjugate (ADC), a targeted therapy, or other anticancer drugs. Anti-TIP-1 antibodies can be used to construct bispecific antibodies with partner mAbs against PD-1, PD-L1, LAG3, TIM-3, CTLA-4, EGFR, HER-2, CD19, CD20, CD33, CD73, CD47, CD3, apelin, DLL-3, CLDN18.2, folate receptor alpha (FOLR1), and/or other tumor surface antigens to treat cancers/tumors that express both CLDN18.2 and the specific tumor associated antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of TIP-1 in a subject. The methods comprise (a) obtaining a sample from the subject; (b) contacting the sample with a monoclonal antibody or antigen-binding fragment thereof of the invention; and (c) determining a level of TIP-1 in the subject.

As used herein, "sample" refers to a biological sample isolated from a subject and can include, but is not limited to, whole blood, serum, plasma, blood cells, endothelial cells, tissue biopsies (e.g., a cancer tissue), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma.

In certain embodiments, the level of TIP-1 in the subject can be determined utilizing assays selected from, but not limited to, a Western blot assay, an ELISA assay, and/or an immunohistochemistry (IHC). Relative protein levels can be determined by utilizing Western blot analysis and immunohistochemistry (IHC), and absolute protein levels can be determined by utilizing an ELISA assay. When determining the relative levels of TIP-1, the levels of TIP-1 can be determined between at least two samples, e.g., between samples from the same subject at different time points, between samples from different tissues in the same subject, and/or between samples from different subjects. Alternatively, when determining absolute levels of TIP-1, such as by an ELISA assay, the absolute level of TIP-1 in the sample can be determined by creating a standard for the ELISA assay prior to testing the sample. A person skilled in the art would understand which analytical techniques to utilize to determine the level of TIP-1 in a sample from the subject utilizing the antibodies or antigen-binding fragments thereof of the invention.

Utilizing methods of determining a level of TIP-1 in a sample from a subject can lead to the diagnosis of abnormal (elevated, reduced, or insufficient) TIP-1 levels in a disease and making appropriate therapeutic decisions. Such a disease can include, for example, cancer. Additionally, by monitoring the levels of TIP-1 in a subject, the risk of developing a disease as indicated above can be determined based on the knowledge of the level of TIP-1 in a particular disease and/or during the progression of the particular disease Embodiments This invention provides the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of:
 a. SEQ ID NOs:3, 4, 5, 6, 7, and 8, respectively;
wherein the antibody or antigen-binding fragment thereof specifically binds TIP-1, preferably human TIP-1.

Embodiment 2 is the isolated monoclonal antibody or antigen-binding fragment thereof of embodiment 1, comprising a heavy chain variable region having a polypeptide sequence at least 95% identical to SEQ ID NO:1, or a light chain variable region having a polypeptide sequence at least 95% identical to SEQ ID NO:2.

Embodiment 3 is the isolated monoclonal antibody or antigen-binding fragment thereof of embodiment 1 or 2, comprising:
 a. a heavy chain variable region having the polypeptide sequence of SEQ ID NO:1, and a light chain variable region having the polypeptide sequence of SEQ ID NO:2;

Embodiment 4 is the isolated monoclonal antibody or antigen-binding fragment thereof of any one of embodiments 1-3, wherein the monoclonal antibody or antigen-binding fragment thereof is capable of inducing effector-mediated tumor cell lysis.

Embodiment 5 is the isolated monoclonal antibody or antigen-binding fragment thereof of any one of embodiments 1-4, wherein the antibody or antigen-binding fragment thereof is chimeric.

Embodiment 6 is the isolated monoclonal antibody or antigen-binding fragment thereof of any one of embodiments 1-5, wherein the antibody or antigen-binding fragment thereof is human or humanized.

Embodiment 7 is an isolated nucleic acid encoding the monoclonal antibody or antigen-binding fragment thereof of any one of embodiments 1-6.

Embodiment 8 is a vector comprising the isolated nucleic acid of embodiment 7.

Embodiment 9 is a host cell comprising the vector of embodiment 8.

Embodiment 10 is a pharmaceutical composition, comprising the isolated monoclonal antibody or antigen-binding fragment thereof of any one of embodiments 1-6 and a pharmaceutically acceptable carrier.

Embodiment 11 is a method of treating cancer in a subject in need thereof, comprising administering to the subject the pharmaceutical composition of embodiment 10.

Embodiment 12 is a method of targeting TIP-1 on a cancer cell surface in a subject in need thereof, the method comprising administering to the subject the pharmaceutical composition of embodiment 10.

Embodiment 13 is a method of producing the monoclonal antibody or antigen-binding fragment thereof of any one of embodiments 1-6, comprising culturing a cell comprising a nucleic acid encoding the monoclonal antibody or antigen-binding fragment thereof under conditions to produce the monoclonal antibody or antigen-binding fragment thereof, and recovering the antibody or antigen-binding fragment thereof from the cell or culture.

Embodiment 14 is a method of producing a pharmaceutical composition comprising the monoclonal antibody or antigen-binding fragment of any one of embodiments 1-6, comprising combining the monoclonal antibody or antigen-binding fragment thereof with a pharmaceutically acceptable carrier to obtain the pharmaceutical composition.

Embodiment 15 is a method of determining a level of TIP-1 in a subject, the method comprising:
 a. obtaining a sample from the subject;
 b. contacting the sample with an isolated monoclonal antibody or antigen-binding fragment thereof of any one of claims 1-6; and
 c. determining a level of TIP-1 in the subject.

Embodiment 16 is the method of embodiment 15, wherein the sample is a tissue sample.

Embodiment 17 is the method of embodiment 16, wherein the tissue sample is a cancer tissue sample.

Embodiment 18 is the method of claim 15, wherein the sample is a blood sample.

EXAMPLES

Example 1: Identification of Anti-TIP-1 Monoclonal Antibodies

Mice were immunized with a fusion protein containing the glutathione S-transferases (GST) and TIP-1 (GST-TIP-1) and boosted with another fusion protein containing a HIS tag, diphtheria toxin A fragment (DTA), and TIP-1 (His-DTA-TIP-1). Plasma titer was determined by ELISA. After euthanization, lymph nodes were collected to produce hybridomas. Hybridomas were grown in 96-well tissue culture plates and supernatants from individual wells were screened by ELISA using GST-TIP-1 for positive signals and GST for counter-screening. The positive hits were confirmed by ELISA with Myc-DDK tagged TIP-1 (TIP1-Myc-DDK). Top positive clones were isolated and sequenced.

Sequences of heavy and light chain variable regions for anti-TIP-1 monoclonal antibody T2 are provided in Tables 1 and 2, and the CDR regions for the anti-TIP-1 monoclonal antibody T2 are provided in Tables 3 and 4.

TABLE 1

Sequences of heavy chain variable region for anti-TIP-1 mAb

| mAb clones | VH |
|---|---|
| T2 | EVKLEQSGPELKKPGETVKISCKASGYTFTDYSMHWVKQAPGKGLKWMGWINTKTRKPTYADDFKGRFAFSLETSARTAYLQINNLKNEDTATYFCAPTGLDYWGQGTSVTVSS (SEQ ID NO: 1) |

VH: heavy chain variable region

TABLE 2

Sequences of light chain variable region for anti-TIP-1 mAb

| mAb clones | VL |
|---|---|
| T2 | DIVITQTTLTLSVSIGQPASISCKSSQSLLDSDGKTYLNWLLQRPGQSPKRLIYLVSKLDSGVPDRFTGSGSGTDFTLKISRVEAEDLGVYYCWQGTHFPRTFGGGTKLEIK (SEQ ID NO: 2) |

VL: light chain variable region

TABLE 3

CDR regions 1-3 of heavy chain for anti-TIP-1 mAb

| mAb clones | HC CDR1 (SEQ ID NO:) | CDR2 (SEQ ID NO:) | CDR3 (SEQ ID NO:) |
|---|---|---|---|
| T2 | GYTFTDYS (3) | INTKTRKP (4) | APTGLDY (5) |

HC: heavy chain; CDR: complementarity determining region

The HC CDRs for the anti-TIP-1 mAbs were determined utilizing the IMGT method (Lefranc, M.-P. et al., Nucleic Acids Res. 1999; 27:209-212).

TABLE 4

CDR regions 1-3 of light chain for anti-TIP-1 mAb

| mAb clones | LC CDR1 (SEQ ID NO:) | CDR2 (SEQ ID NO:) | CDR3 (SEQ ID NO:) |
|---|---|---|---|
| T2 | QSLLDSDGKTY (6) | LVS (7) | WQGTHFPRT (8) |

LC: light chain; CDR: complementarity determining region

The LC CDRs for the anti-TIP-1 mAbs were determined utilizing the IMGT method (Lefranc, M.-P. et al., Nucleic Acids Res. 1999; 27:209-212).

Example 2: Production and Purification of mAb T2 from Hybridoma Supernatant and Culture Media from Transfected 293E Cells Mouse anti-TIP-1 mAb T2 was purified from hybridoma media/supernatants using Protein A affinity chromatography. To obtain the recombinant anti-TIP-1 chimeric mAb, the expression vectors containing the mouse VH and VL fused to the constant regions of human IgG1 heavy chain and kappa light chain, respectively, were transiently transfected into 293E cells. The recombinant antibody produced in the suspension of the 293E cells was purified using Protein A affinity chromatography.

Example 3: ELISA Binding Analysis of Purified Antibodies

Figure 1:
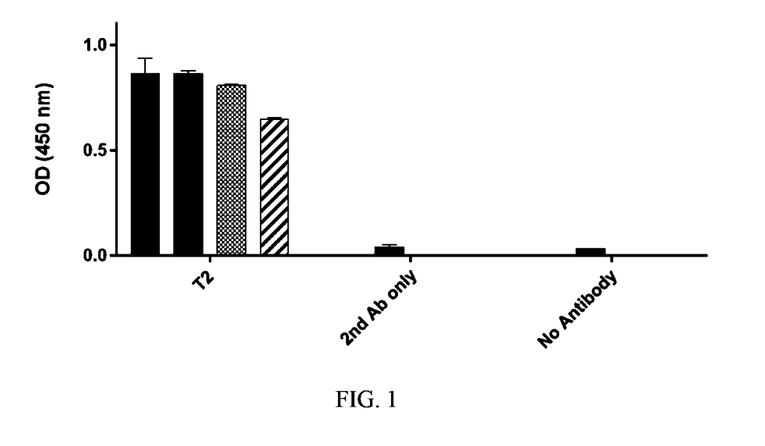
FIG. 1 shows the binding of purified mouse anti-TIP-1 mAb T2 to TIP1-Myc-DDK in an ELISA assay. T2 mAb concentrations used were (from left to right on the graph): 500 ng/ml, 20 ng/ml, 5 ng/ml, and 1 ng/ml, respectively; $2^{nd}$ Ab only, the group was not treated with primary antibodies but treated with HRP-conjugated anti-mouse IgG secondary Abs; No Antibody, neither primary Ab nor $2^{nd}$ Ab was added.
Figure 2:
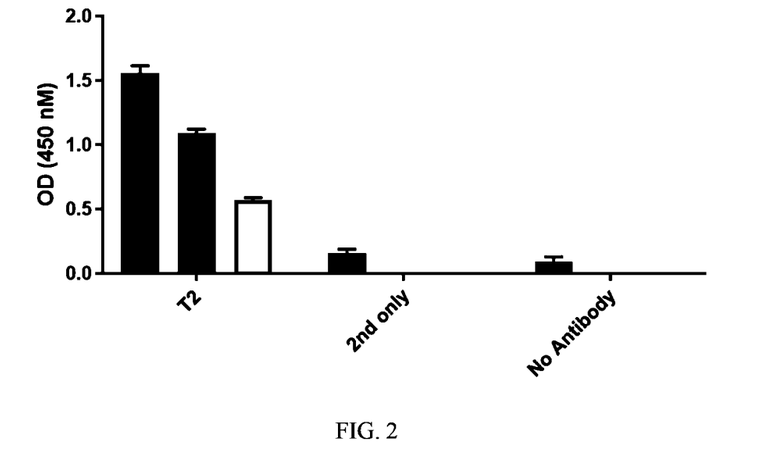
FIG. 2 shows the binding of anti-TIP-1 chimeric mAb (mouse VH and VL fused to the constant regions of human IgG1 and kappa chain, respectively) T2 in an ELISA assay; T2 chimeric mAb concentrations used were (from left to right on the graph): 18 ng/ml, 4 ng/ml, and 1 ng/ml, respectively; $2^{nd}$ Ab only, the group was not treated with primary antibodies but treated with HRP-conjugated anti-human IgG secondary Abs; No Antibody, neither primary Ab nor $2^{nd}$ Ab was added.

TIP1-Myc-DDK in carbonate coating buffer was coated on an ELISA plate at room temperature (50 µL/well at 1 µg/mL) for 1 hr. After washing, ELISA plate was blocked in 5% BSA in PBS for 1 hour and washed again. An anti-TIP-1 mAb was added, mixed and incubated for 60 minutes at room temperature. The plate was washed and the binding of anti-TIP-1 mAb to the immobilized TIP1-Myc-DDK was detected by adding a secondary antibody, an anti-mouse IgG conjugated to horseradish peroxidase (ThermoFisher Scientific, #A16084) or anti-human IgG conjugated to horseradish peroxidase (hIgG-HRP) (ThermoFisher Scientific, #31410), in PBS and incubating for 1 hour and then washed. The ELISA was developed using One-step Detection Solution (ThermoFisher Scientific, Cat #: 34028) and measured as the absorbance at 450 nm. Binding result of the mouse anti-TIP-1 mAb T2 is provided in FIG. 1; T2 mAb concentrations used were (from left to right on the graph): 500 ng/ml, 20 ng/ml, 5 ng/ml, and 1 ng/ml, respectively; $2^{nd}$ Ab only, the group was not treated with primary antibodies but treated with HRP-conjugated anti-mouse IgG secondary Abs; No Antibody, neither primary Ab nor $2^{nd}$ Ab was added). Binding result of the chimeric version of anti-TIP-1 mAb T2 is provided in FIG. 2; T2 mAb concentrations used were (from left to right on the graph): 18 ng/ml, 4 ng/ml, and 1 ng/ml, respectively; $2^{nd}$ Ab only, the group was not treated with primary antibodies but treated with HRP-conjugated anti-mouse IgG secondary Abs; No Antibody, neither primary Ab nor $2^{nd}$ Ab was added.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. An isolated monoclonal antibody or antigen-binding fragment thereof comprising a heavy chain variable region comprising a heavy chain complementarity determining region 1 (HCDR1), HCDR2, and HCDR3, and a light chain variable region comprising a light chain complementarity determining region 1 (LCDR1), LCDR2, and LCDR3, having the polypeptide sequences of
SEQ ID NOs:3, 4, 5, 6, 7, and 8, respectively;
wherein the antibody or antigen-binding fragment thereof specifically binds TIP-1.

2. The isolated monoclonal antibody or antigen-binding fragment thereof of claim 1, comprising a heavy chain variable region having a polypeptide sequence at least 95% identical to SEQ ID NO:1 and a light chain variable region having a polypeptide sequence at least 95% identical to SEQ ID NO:2.

3. The isolated monoclonal antibody or antigen-binding fragment thereof of claim 1, comprising:
a. a heavy chain variable region having the polypeptide sequence of SEQ ID NO:1, and a light chain variable region having the polypeptide sequence of SEQ ID NO:2.

4. The isolated monoclonal antibody or antigen-binding fragment thereof of claim 1, wherein the monoclonal antibody or antigen-binding fragment thereof is capable of inducing effector-mediated tumor cell lysis.

5. The isolated monoclonal antibody or antigen-binding fragment thereof of claim 1, wherein the antibody or antigen-binding fragment thereof is chimeric or humanized.

6. A pharmaceutical composition, comprising the isolated monoclonal antibody or antigen-binding fragment thereof of claim 1 and a pharmaceutically acceptable carrier.

7. An isolated bispecific antibody or antigen-binding fragment thereof comprising the monoclonal antibody or antigen-binding fragment thereof of claim 1.

8. A pharmaceutical composition comprising the isolated bispecific antibody or antigen-binding fragment thereof of claim 7 and a pharmaceutically acceptable carrier.

9. A method of determining a level of TIP-1 in a subject, the method comprising:
a. obtaining a sample from the subject;
b. contacting the sample with an isolated monoclonal antibody or antigen-binding fragment thereof of claim 1; and
c. determining a level of TIP-1 in the subject.

10. The method of claim 9, wherein the sample is a tissue sample or a blood sample.

11. The method of claim 10, wherein the tissue sample is a cancer tissue sample.

* * * * *

SEQUENCE LISTING

<160> NUMBER OF SEQ ID NOS: 9

<210> SEQ ID NO 1
<211> LENGTH: 114
<212> TYPE: PRT
<213> ORGANISM: Artificial Sequence
<220> FEATURE:
<223> OTHER INFORMATION: T2 Heavy Chain Variable Region

<400> SEQUENCE: 1

Glu Val Lys Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
            35                  40                  45

Gly Trp Ile Asn Thr Lys Thr Arg Lys Pro Thr Tyr Ala Asp Asp Phe
        50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Thr Ala Thr Tyr Phe Cys
                85                  90                  95

Ala Pro Thr Gly Leu Asp Tyr Trp Gly Gln Gly Thr Ser Val Thr Val
                100                 105                 110

Ser Ser

<210> SEQ ID NO 2
<211> LENGTH: 112
<212> TYPE: PRT
<213> ORGANISM: Artificial Sequence
<220> FEATURE:
<223> OTHER INFORMATION: T2 Light Chain Variable Region

<400> SEQUENCE: 2

Asp Ile Val Ile Thr Gln Thr Thr Leu Thr Leu Ser Val Ser Ile Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
                100                 105                 110

<210> SEQ ID NO 3
<211> LENGTH: 8
<212> TYPE: PRT
<213> ORGANISM: Artificial Sequence
<220> FEATURE:
<223> OTHER INFORMATION: T2 HC CDR1

<400> SEQUENCE: 3

Gly Tyr Thr Phe Thr Asp Tyr Ser
1               5

<210> SEQ ID NO 4
<211> LENGTH: 8
<212> TYPE: PRT
<213> ORGANISM: Artificial Sequence
<220> FEATURE:
<223> OTHER INFORMATION: T2 HC CDR2

<400> SEQUENCE: 4

Ile Asn Thr Lys Thr Arg Lys Pro
1               5

<210> SEQ ID NO 5
<211> LENGTH: 7
<212> TYPE: PRT
<213> ORGANISM: Artificial Sequence
<220> FEATURE:
<223> OTHER INFORMATION: T2 HC CDR3

<400> SEQUENCE: 5

Ala Pro Thr Gly Leu Asp Tyr
1               5

<210> SEQ ID NO 6
<211> LENGTH: 11
<212> TYPE: PRT
<213> ORGANISM: Artificial Sequence
<220> FEATURE:
<223> OTHER INFORMATION: T2 LC CDR1

<400> SEQUENCE: 6

Gln Ser Leu Leu Asp Ser Asp Gly Lys Thr Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: T2 LC CDR2

<400> SEQUENCE: 7

Leu Val Ser
1

<210> SEQ ID NO 8
<211> LENGTH: 9
<212> TYPE: PRT
<213> ORGANISM: Artificial Sequence
<220> FEATURE:
<223> OTHER INFORMATION: T2 LC CDR3

<400> SEQUENCE: 8

Trp Gln Gly Thr His Phe Pro Arg Thr
1               5

<210> SEQ ID NO 9
<211> LENGTH: 124
<212> TYPE: PRT
<213> ORGANISM: Homo sapiens

<400> SEQUENCE: 9

Met Ser Tyr Ile Pro Gly Gln Pro Val Thr Ala Val Val Gln Arg Val
1               5                   10                  15

Glu Ile His Lys Leu Arg Gln Gly Glu Asn Leu Ile Leu Gly Phe Ser
                20                  25                  30

-continued

```
Ile Gly Gly Gly Ile Asp Gln Asp Pro Ser Gln Asn Pro Phe Ser Glu
        35              40              45
Asp Lys Thr Asp Lys Gly Ile Tyr Val Thr Arg Val Ser Glu Gly Gly
    50              55              60
Pro Ala Glu Ile Ala Gly Leu Gln Ile Gly Asp Lys Ile Met Gln Val
65              70              75              80
Asn Gly Trp Asp Met Thr Met Val Thr His Asp Gln Ala Arg Lys Arg
            85              90              95
Leu Thr Lys Arg Ser Glu Glu Val Val Arg Leu Leu Val Thr Arg Gln
            100             105             110
Ser Leu Gln Lys Ala Val Gln Gln Ser Met Leu Ser
        115             120
```